United States Patent [19]

Sanghvi et al.

[11] Patent Number: 5,676,692
[45] Date of Patent: Oct. 14, 1997

[54] FOCUSSED ULTRASOUND TISSUE TREATMENT METHOD

[75] Inventors: Narendra T. Sanghvi; Richard Bihrle, both of Indianapolis, Ind.; Francis J. Fry, Port Charlotte, Fla.

[73] Assignee: Indianapolis Center for Advanced Research, Inc., Indianapolis, Ind.

[21] Appl. No.: 623,562

[22] Filed: Mar. 28, 1996

[51] Int. Cl.$^6$ ..................................... A61B 8/00
[52] U.S. Cl. ............... 607/97; 607/96; 607/105; 607/113
[58] Field of Search ............... 607/96, 97, 113, 607/114, 105; 128/660.03

[56] References Cited

U.S. PATENT DOCUMENTS

| | | |
|---|---|---|
| 4,586,512 | 5/1986 | Do-huu et al. . |
| 4,620,546 | 11/1986 | Aida et al. . |
| 4,658,828 | 4/1987 | Dory . |
| 4,664,121 | 5/1987 | Sanghvi et al. . |
| 4,858,613 | 8/1989 | Fry et al. . |
| 4,951,653 | 8/1990 | Fry et al. . |
| 4,955,365 | 9/1990 | Fry et al. . |
| 5,036,855 | 8/1991 | Fry et al. . |
| 5,054,470 | 10/1991 | Fry et al. . |
| 5,080,102 | 1/1992 | Dory ................... 607/96 |
| 5,149,319 | 9/1992 | Unger . |
| 5,215,680 | 6/1993 | D'Arrigo . |
| 5,219,401 | 6/1993 | Cathignol et al. . |
| 5,234,004 | 8/1993 | Hascoet et al. .......... 128/660.03 |
| 5,247,935 | 9/1993 | Cline et al. .............. 607/96 |
| 5,330,518 | 7/1994 | Neilson et al. .......... 607/113 |
| 5,409,006 | 4/1995 | Buchholtz et al. ...... 607/96 |
| 5,470,350 | 11/1995 | Buchholtz et al. ...... 128/660.03 |
| 5,474,071 | 12/1995 | Chapelon et al. ....... 128/660.03 |
| 5,480,417 | 1/1996 | Hascoet et al. ......... 607/113 |

*Primary Examiner*—Lee S. Cohen
*Assistant Examiner*—Stephen Huang
*Attorney, Agent, or Firm*—Barnes & Thornburg

[57] ABSTRACT

A method of treatment of tissue with focussed ultrasound comprises placing adjacent the tissue to be treated a reflector of ultrasound or an ultrasound energy conversion device which converts received ultrasound energy to heat, stores the heat and then releases the heat over time into the tissue to be treated. An ultrasound transducer is then oriented with its focal point adjacent the reflector or ultrasound energy conversion device. The tissue is then irradiated with high intensity focussed ultrasound while the reflector or ultrasound energy conversion device is in place.

12 Claims, 4 Drawing Sheets

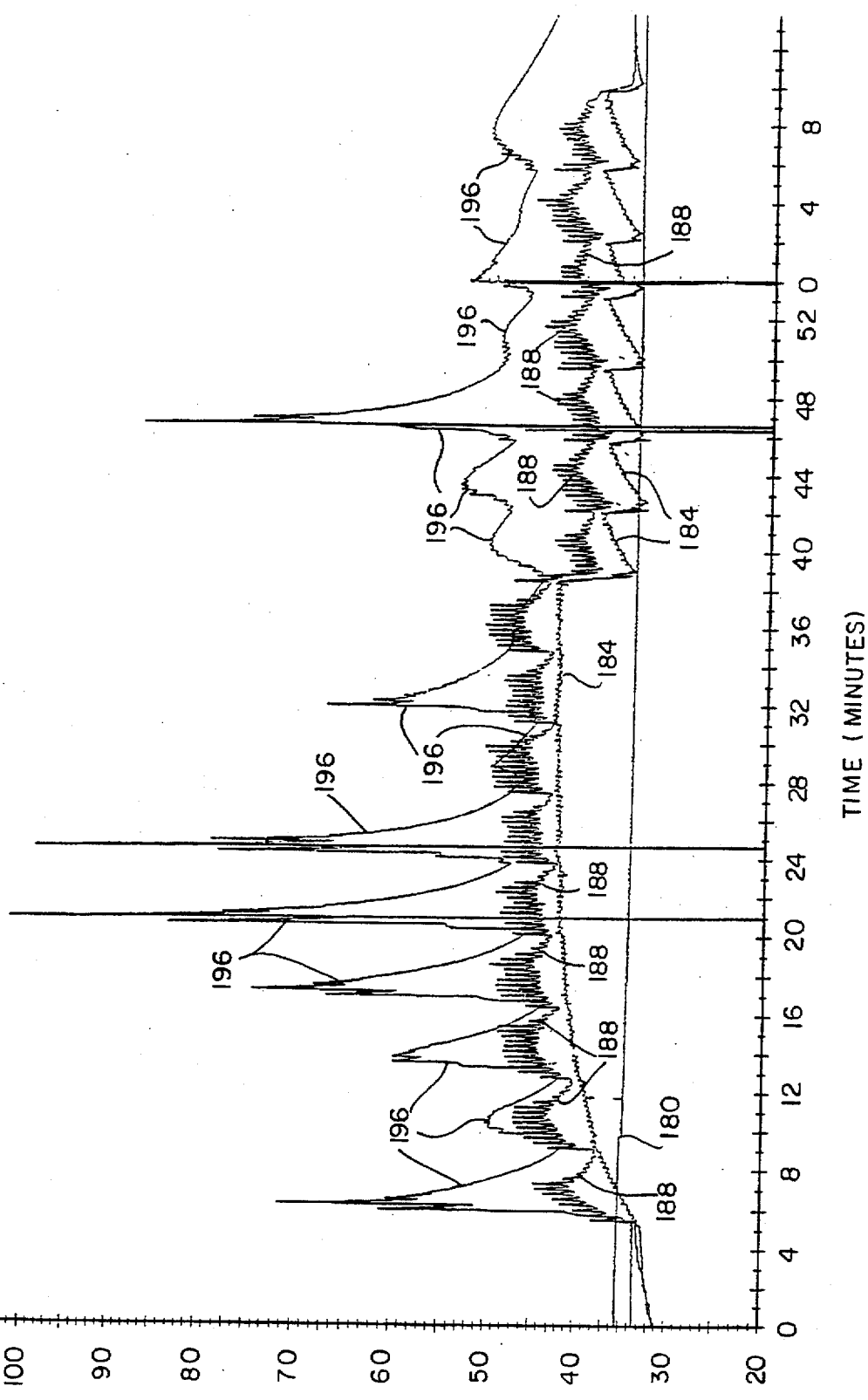

FOCUSSED ULTRASOUND TISSUE TREATMENT METHOD

BACKGROUND OF THE INVENTION

This invention relates to ultrasound tissue ablation. It is disclosed in the context of prostate ablation, but it is believed to be useful in other applications as well.

The efficacy of ultrasound as a medium for non-invasive or minimally invasive tissue removal has been established. There are, for example the disclosures of U.S. Pat. Nos.: 4,586,512; 4,620,546; 4,658,828; 4,858,613; 4,951,653; 4,955,365; 5,036,855; 5,054,470; 5,149,319; 5,215,680; and, 5,219,401. No representation is intended hereby that a thorough search of all material prior art has been conducted or that no more material prior art exists. Nor should any such representation be inferred.

In some applications, however, some portion of the transmitted ultrasound energy is not applied to optimal effect. For example, it is known that in the transrectal ultrasound ablation of prostate tissue, such as in the treatment of benign prostatic hyperplasia (BPH), the posterior lesion (that is, the lesion that forms between the depth at which the urethra passes through the prostate and the posterior surface of the prostate) is much more effective in relieving the symptoms of BPH than the anterior lesion (the lesion that forms between the depth at which the urethra passes through the prostate and the anterior surface of the prostate). In this sense, the ultrasound energy that results in the anterior lesion is "wasted," although the anterior lesion is formed. If this energy could be reflected back posteriorly for integration with the energy that is absorbed by the posterior prostate, the effectiveness of the ultrasound ablation treatment at relieving BPH symptoms would be enhanced.

SUMMARY OF THE INVENTION

Accordingly it is an object of this invention to provide methods and apparatus by which the effectiveness of ultrasound as a medium for tissue ablation is enhanced.

According to an aspect of the invention, a method of treatment of tissue with focussed ultrasound comprises placing adjacent the tissue to be treated a reflector of ultrasound, orienting an ultrasound transducer with its focal point adjacent the reflector and then irradiating the tissue with focussed ultrasound while the reflector is in place.

According to another aspect of the invention, a method of treatment of tissue with focussed ultrasound comprises placing adjacent the tissue to be treated an ultrasound energy conversion device which converts received ultrasound energy to heat, stores the heat and then releases the heat over time into the tissue to be treated. An ultrasound transducer is oriented with its focal point adjacent the ultrasound energy conversion device. The tissue is then irradiated with focussed ultrasound while the ultrasound energy conversion device is in place.

Illustratively, the step of placing adjacent the tissue to be treated a reflector of ultrasound or an ultrasound energy conversion device comprises the step of inserting a catheter comprising an ultrasound reflective material or ultrasound energy converting and heat storage material into a body lumen or orifice which lies adjacent the tissue to be treated.

Additionally illustratively, the step of inserting a catheter comprising an ultrasound reflective material or an ultrasound energy converting and heat storage material into a body lumen or orifice comprises the step of inserting a catheter containing red rubber into the body lumen or orifice.

Further illustratively, the step of inserting a catheter comprising an ultrasound reflective material or ultrasound energy converting and heat storage material into a body lumen or orifice which lies adjacent the tissue to be treated comprises the steps of inserting a balloon catheter into the urethra to the depth of the bladder and inflating the balloon in the bladder.

Additionally illustratively, the step of irradiating the tissue with ultrasound comprises irradiating the prostate with the high intensity focussed ultrasound.

Further illustratively, the step of orienting the ultrasound transducer with its focal point adjacent the reflector comprises the step of coupling the transducer through the rectal wall.

BRIEF DESCRIPTION OF THE DRAWINGS

The invention may best be understood by referring to the following description and accompanying drawings which illustrate the invention. In the drawings:

FIG. 5 illustrates temperature profiles obtained with a system constructed and operated in accordance with the teachings of FIGS. 2–4.

DETAILED DESCRIPTION OF THE ILLUSTRATIVE EMBODIMENT

Figure 1:
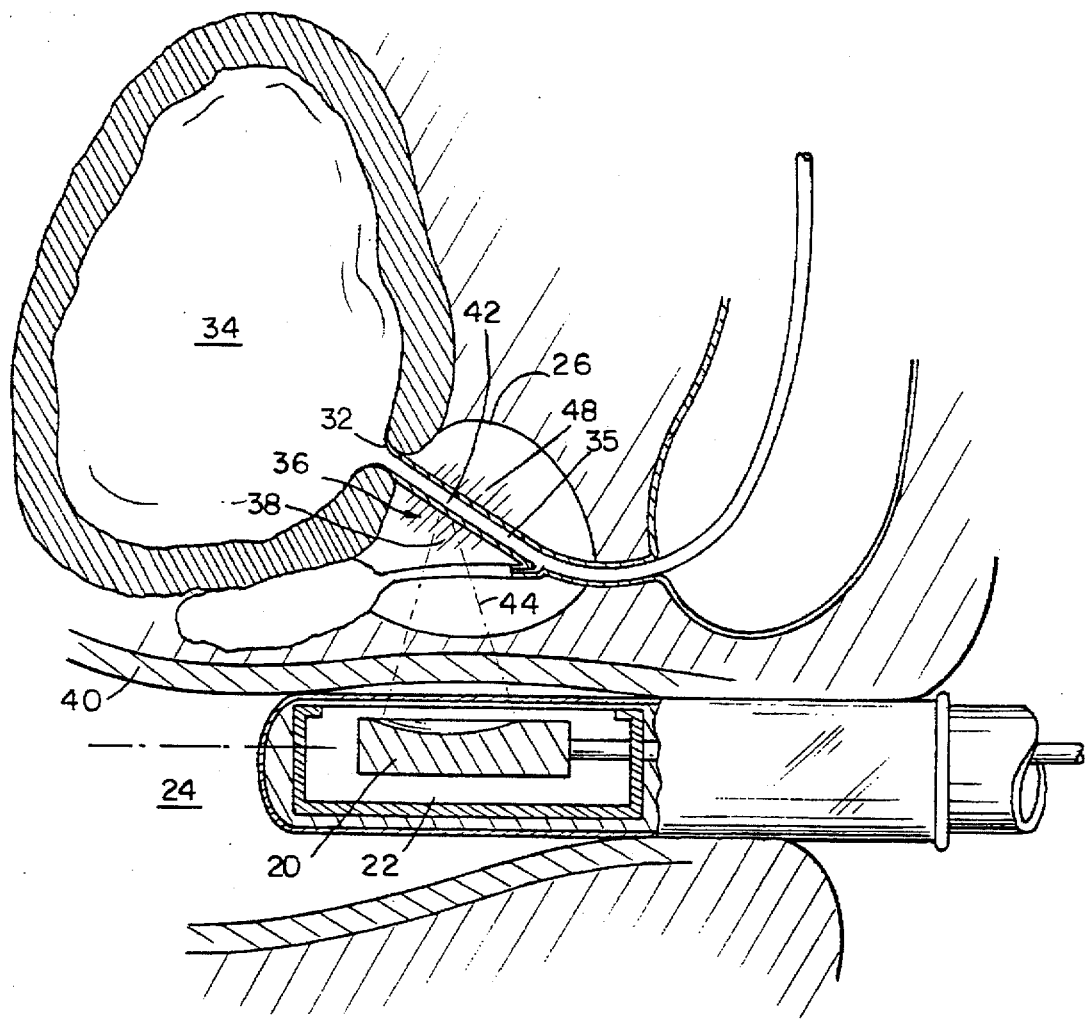
FIG. 1 illustrates a step in the prior art transrectal high intensity focussed ultrasound (HIFU) ablation of a diseased prostate.

A limitation on the effectiveness of HIFU as a treatment for BPH can best be appreciated by referring to FIG. 1. An ultrasound transducer 20 in a coupling fluid 22 is inserted into the colon 24 of a sufferer of BPH directly behind the affected prostate 26. Numerous techniques for visualization of this region are known. Many systems for visualization employ the same transducer 20 in a low power, visualization mode for visualization of the prostate 26, and in a HIFU mode for subsequent ablation therapy. The visualization is usually accomplished with the aid of a urethral catheter (not shown) having a balloon end and an inflating lumen for inflating the balloon in the neck 32 of the bladder 34 to anchor the catheter. The catheter is visible in the visualizing intensity ultrasound generated by transducer 20.

After the visualization of the neck 32 of the bladder 34, the urethra 35 and surrounding diseased prostate 26 has been completed and the transducer 20 is oriented for treatment of the prostate 26, the balloon is deflated, the catheter is removed and the HIFU treatment of the prostate 26 for BPH commences according to a treatment format established by the treating physician. The lesion 36 which results from the application of the HIFU is somewhat elongated, with a somewhat larger posterior portion 38 of the lesion 36 lying between the rectal wall 40 and the focal zone 42 of the ultrasound beam 44 in the vicinity of (indeed here at) the urethra 35. A somewhat smaller portion 48 of the lesion 36 lies anterior to the urethra 35 toward the lower front of the abdomen. Although the HIFU energy which is absorbed by the prostate 26 anterior to the urethra 35 does result in an anterior lesion 48, the relief of BPH symptoms afforded by the anterior lesion 48 is not as great as the relief afforded by the posterior lesion 38.

Figure 2:
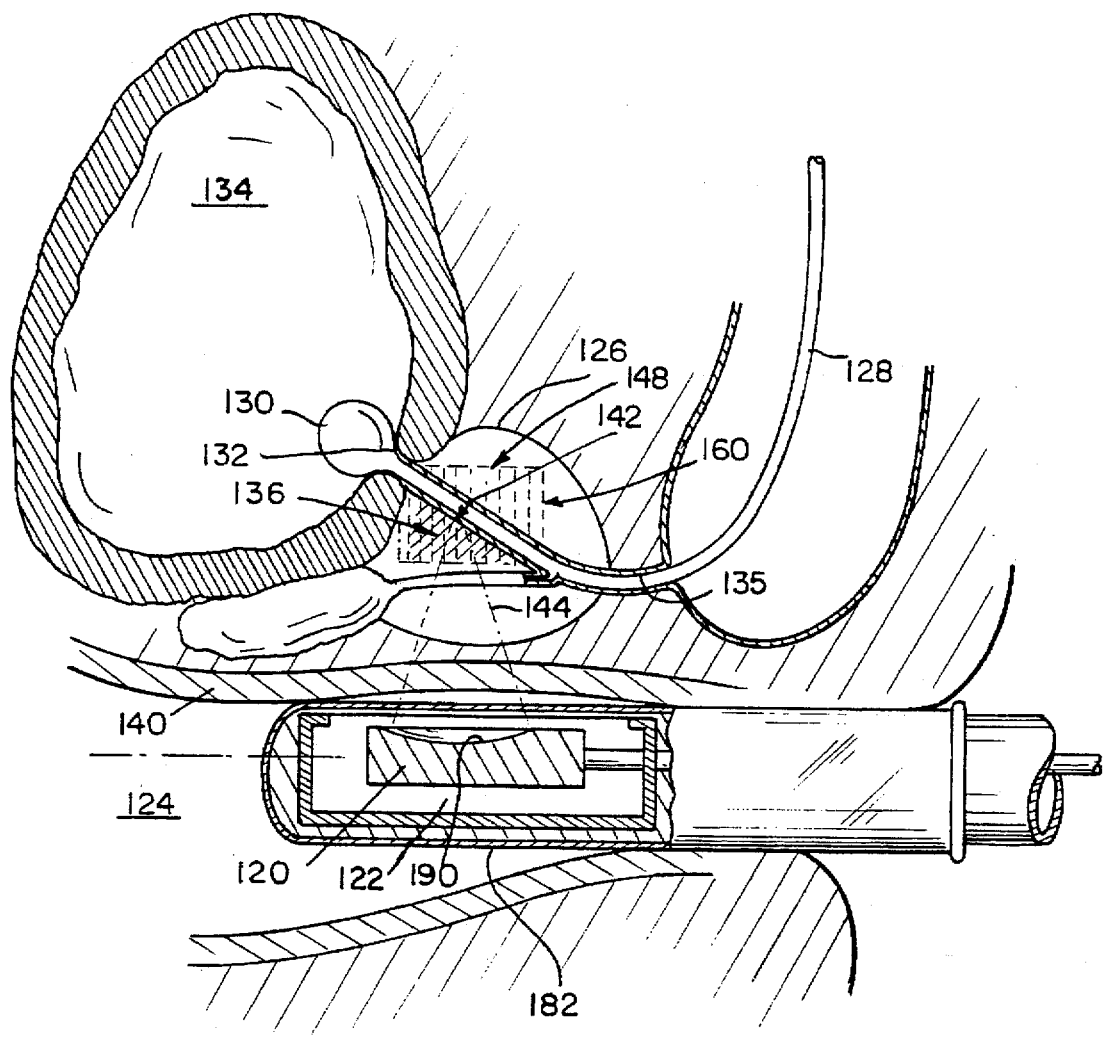
FIG. 2 illustrates a corresponding step to the one illustrated in FIG. 1, but performed according to the present invention.
Figures 3, 4:
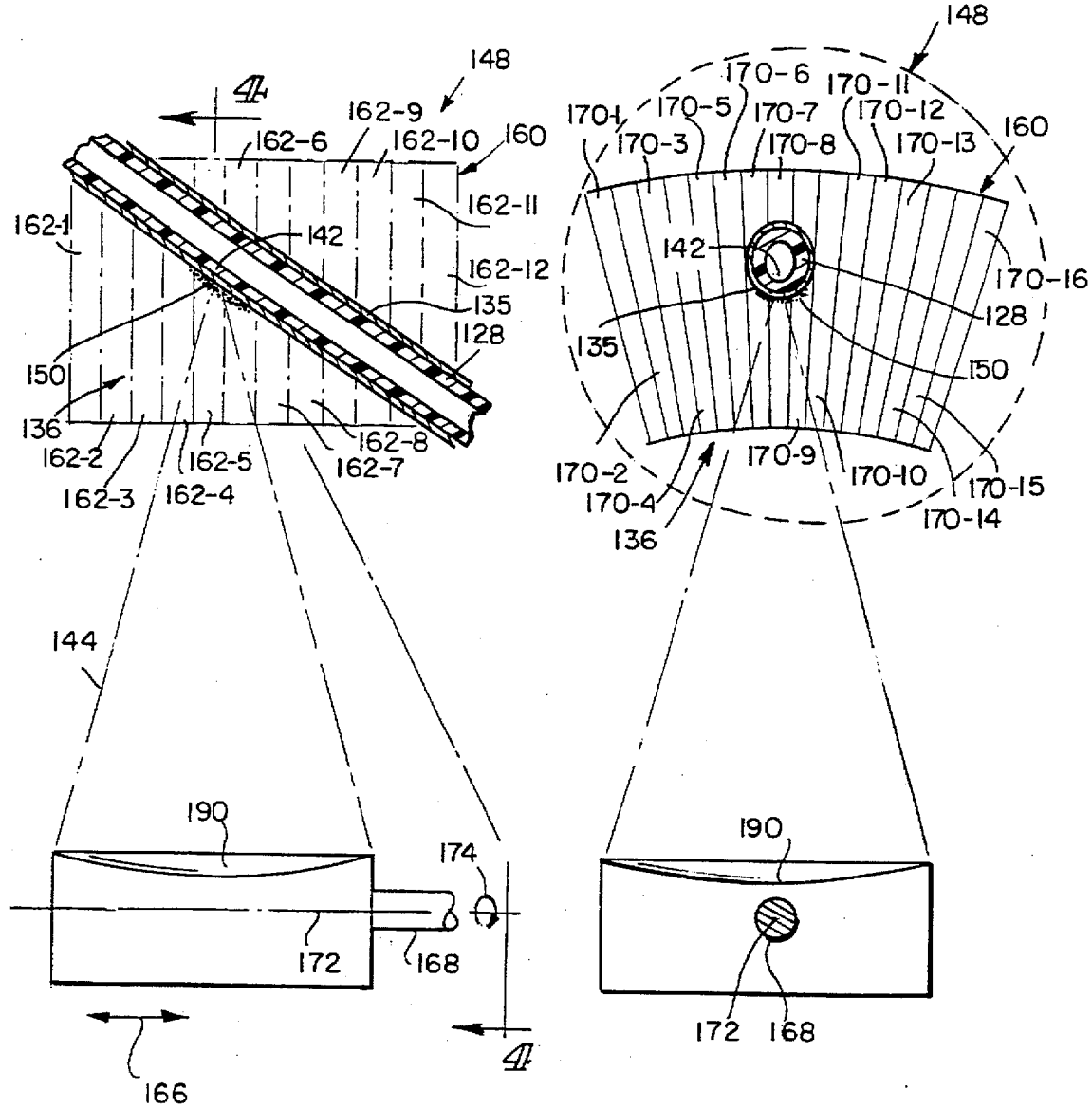
FIG. 3 illustrates a much enlarged view of a detail of the step illustrated in FIG. 2.
FIG. 4 illustrates a view of the detailed illustration in FIG. 3 taken generally along section lines 4—4 of FIG. 3.

Referring now to FIGS. 2, 3 and 4, according to the invention, an ultrasound transducer 120 in a coupling fluid 122 is inserted into the colon 124 of a sufferer of BPH directly behind the affected prostate 126. Visualization of the treatment field is accomplished with the aid of a urethral catheter 128 having a balloon end 130 and an inflating lumen for inflating the balloon 130 in the neck 132 of the bladder 134 and to anchor the catheter 128. The catheter 128 is visible in the visualizing intensity ultrasound for transducer 120. After the visualization of the urethra 135 and surrounding diseased prostate 126 has been completed and the transducer 120 is oriented for treatment of the prostate 126, the catheter 128 is not removed. Rather the HIFU treatment of the prostate 126 for BPH commences with the catheter 128 in place in the urethra 135 according to a treatment format established by the treating physician.

The lesion 136 which results from the application of the HIFU is limited almost exclusively by the presence of catheter 128 to between the rectal wall 140 and the focal zone 142 of the ultrasound beam 144 in the vicinity of the surface of catheter 128. In this way, the HIFU incident on the catheter 128 is reflected posteriorly and combines with the direct HIFU to achieve an effective lesion 136, generally with lower input power to transducer 120. Almost no HIFU energy is transmitted to, or absorbed by, the prostate 126 anterior to the urethra 135. Therefore, there is no "wasted" lesion in region 148. The relief of BPH symptoms is delivered more effectively and with lower input power by limiting the lesion to region 136. This effect is further enhanced by what appears to be cavitation bubble "seeding" of region 136 adjacent catheter 128 and urethra 135. As the HIFU is applied, cavitation bubbles 150 appear readily in this area. The cavitation bubbles trap both some HIFU energy incident on catheter 128 and some HIFU energy reflected from catheter 128, and release this trapped energy back into the posterior lesion prostate tissue as they rupture, enhancing the efficiency of the HIFU at producing the posterior lesion 136. Microscopic imperfections in the outer wall of catheter 128 are believed to contribute to this cavitation bubble enhancement phenomenon.

Various kinds of catheters 128 have been employed. Suitable catheters include Surgicot™ red rubber catheters, Dow Corning Silastic® Foley catheters, Olbert urological catheters, Bardex Foley catheters and Baxter urological catheters.

A suitable treatment format can best be appreciated by referring to FIGS. 2–5. A region of the prostate 126 to be treated is divided into a grid 160, with sections 162-1, 162-2 . . . 162-12 spaced uniformly along the adjacent rectal wall 140 capable of being individually addressed for HIFU treatment by moving the transducer 120 in the directions indicated by double ended arrow 166 into and out of the colon 124. Uniformly angularly spaced sectors 170-1, 170-2 . . . 170-16 are capable of being individually addressed by rotation of the treatment transducer 120 about its axis 172 on drive shaft 168, as indicated by double ended arrow 174. A code wheel (not shown) can be fixed on the shaft 168 for reading the angular orientation of the transducer 120 in accordance with known principles. See, for example, U.S. Pat. No. 4,664,121. In this manner, the tissue of the prostate 126 in the treatment region 160 can be treated, one longitudinal 162-1, . . . 162-12 and angular 170-1, . . . 170-16 sector at a time. Such a treatment format will result in temperature profiles illustrated in FIG. 5. Body temperature is illustrated by curve 180. As will be appreciated body temperature remote from the treatment site 160 is unaffected by the treatment. The temperature of the coupling liquid, in this case, deionized, degassed water in the transducer probe 182 is illustrated by curve 184. The reason for the discontinuity at about 39 minutes of the treatment regimen is that an external coupling liquid circulation circuit (not shown) was activated at that time, resulting in circulation of the coupling liquid through the external circuit and the resultant cooling of the coupling liquid. Curve 188 is a temperature profile of the rectal wall 140. The rectal wall 140 lies in the near field of the treatment transducer 120, that is, between the emitting surface 190 of the treatment transducer 120 and the focal zone 142 of the treatment transducer 120. Curve 196 is a temperature profile of the surface of the catheter 128. The spikes in the various temperature profiles occur when the focal zone 142 is very close to the various thermocouples used to generate the temperature profiles. Curve 196 clearly establishes the efficacy of the treatment method of the present invention employing the HIFU energy conversion, heat retention and heat radiation capability of catheter 128 when catheter 128 is left in place during the HIFU treatment.

Because the treatment thermal dosage is proportional to $\Sigma T \Delta t$ at where T is any elevated temperature at which tissue is maintained and $\Delta t$ is the time during which the tissue is maintained at that temperature, raising the temperature of the tissue-catheter 128 surface interface, both by ultrasound absorption and reradiation, and by reflection of ultrasound, will assure more complete tissue destruction.

The above-noted materials are illustrative of materials that absorb ultrasound, convert it into heat and store and radiate the heat into the surrounding tissue. Polymers generally are noted for exhibiting these same characteristics, that is, enhanced effects of HIFU exposure of tissue. These effects can be further augmented by the use of Albunex or other microbubble or microbubble production-enhancing materials. These materials can be used to enhance cavitation of liquids in the tissue, making the benefits of cavitation as a tissue ablation mechansim more accessible at lower applied HIFU power densities. Additionally, the presence of the red rubber, Silastic®, and other polymer material catheters 128 promotes cavitation even without the present of other cavitation-inducing agents at much lower applied HIFU powers (sometimes reduced by half or more). The mismatched foreign material and tissue acoustic impedances produce larger reflected energy as well, accounting for some of the enhanced tissue ablation demonstrated by the presence of these foreign material catheters 128 in the urethra 135. The foreign material provides an enhanced environment for cavitation at the foreign material-tissue interface. The increased energy released at this interface gives rise to higher pressure and shock waves, disintegrating the tissue and mechanically destroying the tissue in a predictable manner. This promotes sloughing off of the tissue in the treatment zone 136, providing more immediate and lasting relief of BPH symptoms.

Also, when the transducer 120 is being used in the visualization mode, because lower applied power can induce cavitation and because cavitation bubbles are extremely echogenic, the treatment site 136 is much more readily visualized with the foreign object 128 in place. With the foreign object 128 in place in the body, differences in ultrasound tissue absorption coefficients become much less critical in the application of sufficient HIFU to achieve ablation. Thus, the effects of variations in the tissues encountered in the near field between the transducer 120 and the focal zone 142 in a patient, or from patient to patient, on patient treatment regimens and formats are reduced.

What is claimed is:

1. A method of treatment of tissue with focussed ultrasound comprising placing adjacent the tissue to be treated a reflector of ultrasound, orienting an ultrasound transducer with its focal point adjacent the reflector and then irradiating the tissue with focussed ultrasound while the reflector is in place the reflector reflecting energy into the tissue to aid the focussed ultrasound in treating the tissue.

2. The method of claim 1 wherein the step of placing adjacent the tissue to be treated a reflector of ultrasound comprises the step of inserting a catheter comprising an ultrasound reflective material into a body lumen or orifice which lies adjacent the tissue to be treated.

3. The method of claim 2 wherein the step of inserting a catheter comprising an ultrasound reflective material into a body lumen or orifice comprises the step of inserting a catheter containing red rubber into the body lumen or orifice.

4. The method of claim 2 wherein the step of inserting a catheter comprising an ultrasound reflective material into a body lumen or orifice which lies adjacent the tissue to be treated comprises the steps of inserting a balloon catheter into urethra to the depth of bladder and inflating the balloon in the bladder.

5. The method of claim 4 wherein the step of irradiating the tissue with ultrasound comprises irradiating prostate with the focussed ultrasound.

6. The method of claim 5 wherein the step of orienting the ultrasound transducer with its focal point adjacent the reflector comprises the step of coupling the transducer through rectal wall.

7. A method of treatment of tissue with focussed ultrasound comprising placing adjacent the tissue to be treated an ultrasound energy conversion device which converts received ultrasound energy to heat, stores the heat and then releases the heat over time into the tissue to be treated, orienting an ultrasound transducer with its focal point adjacent the ultrasound energy conversion device and then irradiating the tissue with focussed ultrasound while the ultrasound energy conversion device is in place, the energy conversion device releasing the heat over time into the tissue to be treated, aiding the focussed ultrasound in treating the tissue.

8. The method of claim 7 wherein the step of placing adjacent the tissue to be treated an ultrasound energy conversion device comprises the step of inserting a catheter comprising an ultrasound energy converting material into a body lumen or orifice which lies adjacent the tissue to be treated.

9. The method of claim 8 wherein the step of inserting a catheter comprising an ultrasound energy converting material into a body lumen or orifice comprises the step of inserting a catheter containing red rubber into the body lumen or orifice.

10. The method of claim 8 wherein the step of inserting a catheter comprising an ultrasound energy converting material into a body lumen or orifice which lies adjacent the tissue to be treated comprises the steps of inserting a balloon catheter into urethra to the depth of a bladder and inflating the balloon in the bladder.

11. The method of claim 10 wherein the step of irradiating the tissue with ultrasound comprises irradiating prostate with the focussed ultrasound.

12. The method of claim 11 wherein the step of orienting the ultrasound transducer with its focal point adjacent the ultrasound energy conversion device comprises the step of coupling the transducer through a rectal wall.

* * * * *